United States Patent [19]

Senda et al.

[11] Patent Number: 5,374,766
[45] Date of Patent: Dec. 20, 1994

[54] ESTER AND METHOD FOR PRODUCTION THEREOF AS WELL AS HYDROLYSIS PROCESS AND DETERMINATION OF OPTICAL PURITY USING THIS ESTER

[75] Inventors: Shuji Senda; Eiichiro Fukuzaki; Yutaka Nakazono; Tetsuo Omata, all of Osaka, Japan

[73] Assignee: Nitto Denko Co., Ltd., Ibaraki, Japan

[21] Appl. No.: 828,067

[22] Filed: Jan. 30, 1992

[30] Foreign Application Priority Data

Feb. 28, 1991 [JP] Japan .................. 3-059485

[51] Int. Cl.$^5$ ............................... C07C 69/76
[52] U.S. Cl. ................... 560/106; 560/231; 554/229; 435/280; 23/293 R
[58] Field of Search ............... 554/229; 560/106, 231; 435/280; 23/283 R

[56] References Cited

PUBLICATIONS

Hauser, F. M. et al. J. Am. Chem. Soc. 1984, 106 1862–1863.
Shigefumi Kuwahara and Kenji Mori-Tetrahedron vol. 46, No. 24 pp. 8083–8092, 1990 (Synthesis of Both The Enantiomers of Hauptmann's Periplanone-A and Clarification Of The Structure Of Persoons's Periplanone-A).

*Primary Examiner*—Paul J. Killos
*Attorney, Agent, or Firm*—Joseph C. Mason, Jr.; Ronald E. Smith

[57] ABSTRACT

This invention relates to a novel ester which presents as (CF 1) and a method for the production of the same as well as a process for hydrolysis and a method for the determination of an optical purity using this ester, and the object thereof is to provide an intermediate for the synthesis or various natural products, which has high stability, and the optical purity of which can readily be determined, according to the esterification of 1-oxo-5-hydroxymethyl-2-cyclohexene which is unstable to acids and alkalis.

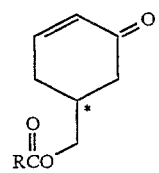

(CF1)

8 Claims, 4 Drawing Sheets

ESTER AND METHOD FOR PRODUCTION THEREOF AS WELL AS HYDROLYSIS PROCESS AND DETERMINATION OF OPTICAL PURITY USING THIS ESTER

FIELD OF THE INVENTION

This invention relates to a novel ester and a method for the production of the same as well as a process for hydrolysis and a method for the determination of an optical purity using this ester, and the object thereof is to provide an intermediate for the synthesis of various natural products, which has high stability, and the optical purity of which can readily be determined, according to the esterification of 1-oxo-5-hydroxymethyl-2-cyclohexene which is unstable to acids and alkalis.

PRIOR ART 5-hydroxy-2-cyclohexanone (CF 3), which is one of the alcohols having an α, β-unsaturated carbonyl group, has hitherto been known as an important intermediate for the synthesis of various natural products. Moreover, (5S)-5-hydroxymethyl-2-cyclohexanone (CF 5), which is one of its optically-active substances, has been found to be an important intermediate for the synthesis of (−)-periplanone-B which is a sex pheromon of Periplaneta Americana (reference name: A. B. Smith, III and Ruth E. Richmond, J. Am. Chem. Soc., 105, 575(1983); S. Kuwahara and K. Mori, Heterocycles, 28, 1(1989)).

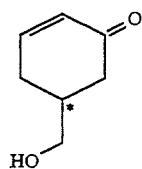

(CF3)

(wherein mark "*" represents an asymmetric carbon atom).

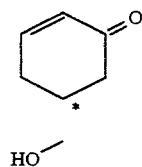

(CF5)

(wherein mark "*" represents an asymmetric carbon atom, and the configuration at position 5 is in the S-form)

However, 1-oxo-5-hydroxymethyl-2-cyclohexene (CF 3), which is one of the alcohols having all α, β-unsaturated carbonyl group, has been a substance which is difficult to utilize because this substance has several disadvantages that it is unstable against acids and bases, and that it is susceptible to deteriorate, etc.

In addition, as a method for measuring the optical purity of 1-oxo-5-hydroxymethyl-2-cyclohexene (CF 3), there has been no other way than the determination by measurement of its angle of rotation. Such a method is lacking for accuracy, and there has been no method for determining the optical purity of optically-active substances for 1-oxo-5-hydroxymethyl-2-cyclohexene (CF 3) with ease and accuracy.

For this reason, many attempts have been made to create derivatives, such as an ester, of 1-oxo-5-hydroxymethyl-2-cyclohexene (CF 3), which have high stability, and the optical purity of which can readily be determined, and which can readily be converted into 1-oxo-5-hydroxymethyl-2-cyclo-hexene (CF 3) that is an important intermediate for the synthesis of various natural products. In actual cases, however, the esterification of 1-oxo-5-hydroxymethyl-2-cyclohexene (CF 3) and the hydrolysis of its ester were difficult because of its instability against acids and bases.

For example, an attempt has been made to esterify 1-oxo-5-hydroxymethyl-2-cyclohexene (CF 3) by a usual process with an acid chloride of the formula RCOCl under the existence or a base such as pyridine. The reaction became complex because it is an unstable substance, and therefore, the desired ester was not obtained.

PROBLEMS TO BE SOLVED BY THE INVENTION

Under these circumstances, it has been desired to create an ester or the like, of 1-oxo-5-hydroxymethyl-2-cyclohexene, which has high stability, and the optical purity of which can readily be determined, and which can readily be converted into 1-oxo-5-hydroxymethyl 2-cyclo-hexene that is an important intermediate for the synthesis of various natural products.

MEANS FOR SOLVING THE PROBLEMS

The novel ester, the method for the production of the same, the process for hydrolysis and the method for the determination of an optical purity using this ester are a novel ester of the general formula (CF 1); a method for the production of the novel ester, characterized in that 1-oxo-5-hydroxymethyl-2-cyclohexene (CF 3) is esterified in an organic solvent with an acid anhydride of the general formula (CF 4) and a lipase; a process for hydrolysis characterized in that the ester (CF 1) is hydrolyzed with a lipase to obtain the 1-oxo-5-hydroxymethyl-2-cyclohexene (CF 3); and a method for the determination of an optical purity, characterized in that the optical purity of the ester (CF 1) is measured to determine the optical purity of the 1-oxo-5-hydroxymethyl-2-cyclohexene (CF 3), respectively, so that all of the problems discussed above can be solved thereby.

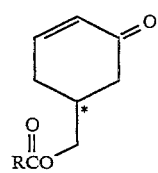

(CF1)

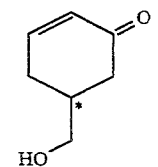

(CF3)

-continued

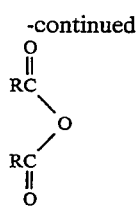
(CF4)

(wherein R is an alkyl group containing 2 to 10 carbon atoms or an aryl group, and mark "*" represents an asymmetric carbon atom).

DETAILED DESCRIPTION OF THE INVENTION

The following will describe the construction of this invention in detail.

The novel ester (CF 1) according to this invention is a novel substance which is a colorless, transparent, oily liquid:

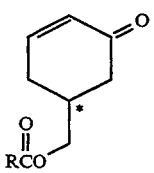
(CF1)

(wherein R is an alkyl group containing 2 to 10 carbon atoms or an aryl group, and mark "*" represents an asymmetric carbon atom).

The results of the atomic analysis with respect to the ester wherein R is C8H7 were as follows: found: C, 67.15%; H, 8.20%; calcd: C, 67.32%; H, 8.22%.

Figure 1:
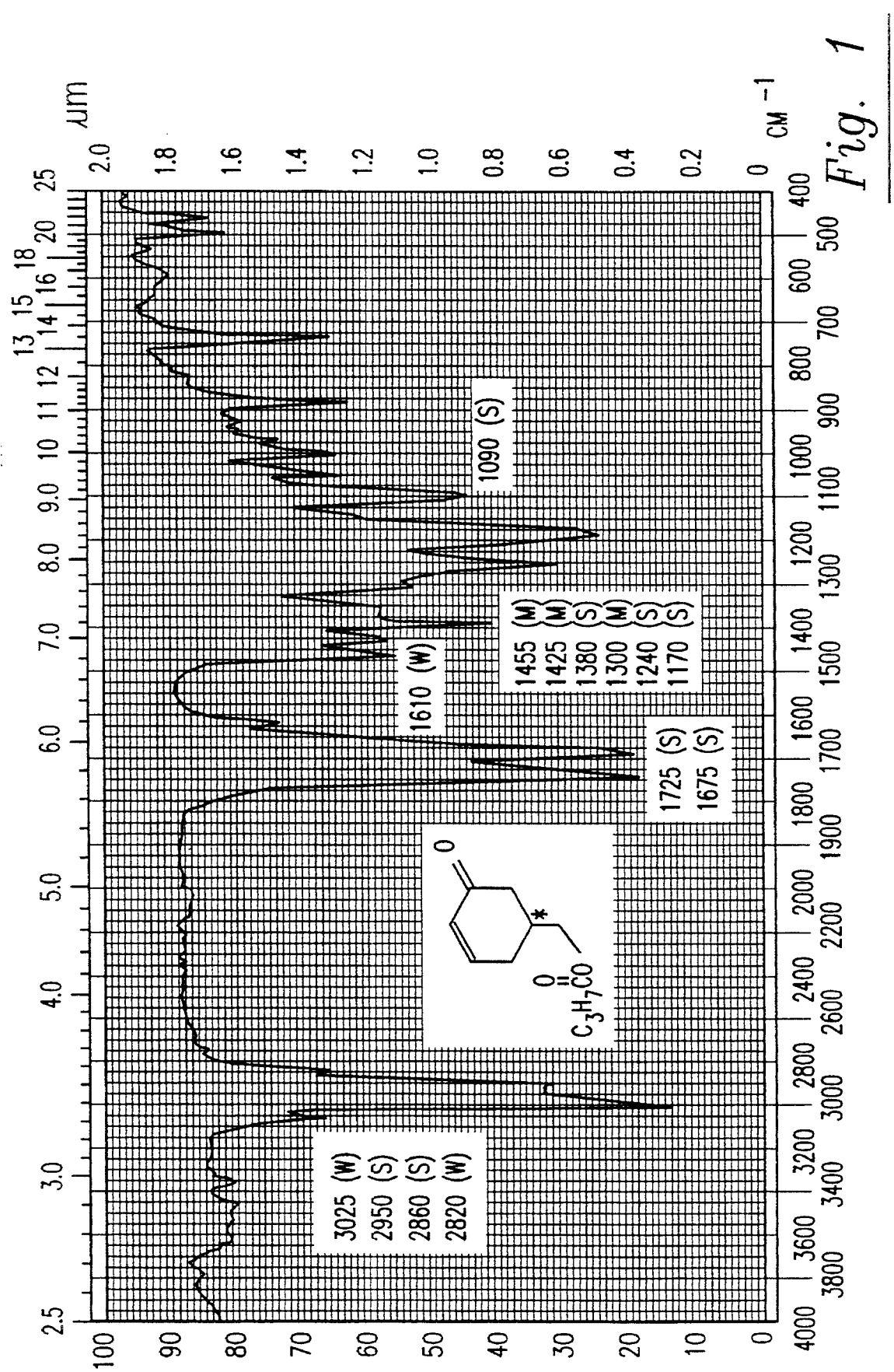
FIG. 1 is a diagram showing the infrared absorption spectrum of 1-oxo-5-butyroyloxymethyl-2-cyclohexene.

Moreover, the absorption wave numbers (cm−1) observed in the infrared absorption spectrum were 3025 (w), 2950 (s), 2860 (s), 2820 (w), 1725 (s), 1675 (s), 1610 (w), 1455 (m), 1425 (m), 1380 (s), 1300 (m), 1240 (s), 1170 (s), and 1090 (s). (See FIG. 1). The measurement was conducted by the thin-film method.

Figure 2:
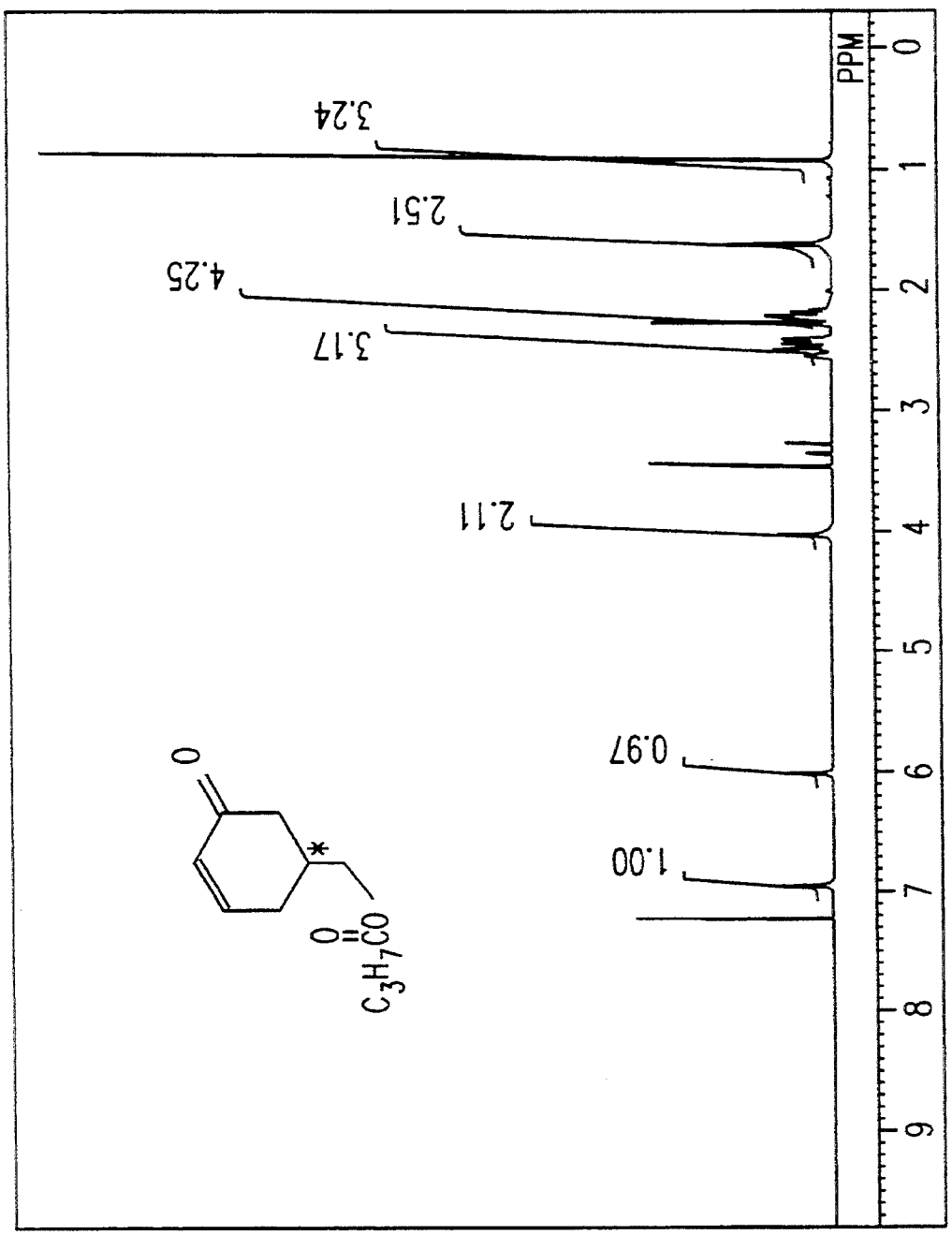
FIG. 2 is a diagram showing the 1 H nuclear magnetic resonance spectrum of 1-oxo-5-butyroyloxymethyl-2-cyclo-hexene.

The δ-values observed in the proton nuclear magnetic resonance spectrum (400 MHz, CDCl3) were 0.936 (3H, t, J=7.3 Hz), 1.641 (2H, tq, J=7.6, 7.6 Hz), 2.12-2.32 (4H, m), 2.40-2.56 (3H, m), 4.40 (2H, dd, J=5.6, 0.5 Hz), 6.02-6.06 (1H, m), and 6.93-6.98 (1H, m). (See FIG. 2).

Figure 3:
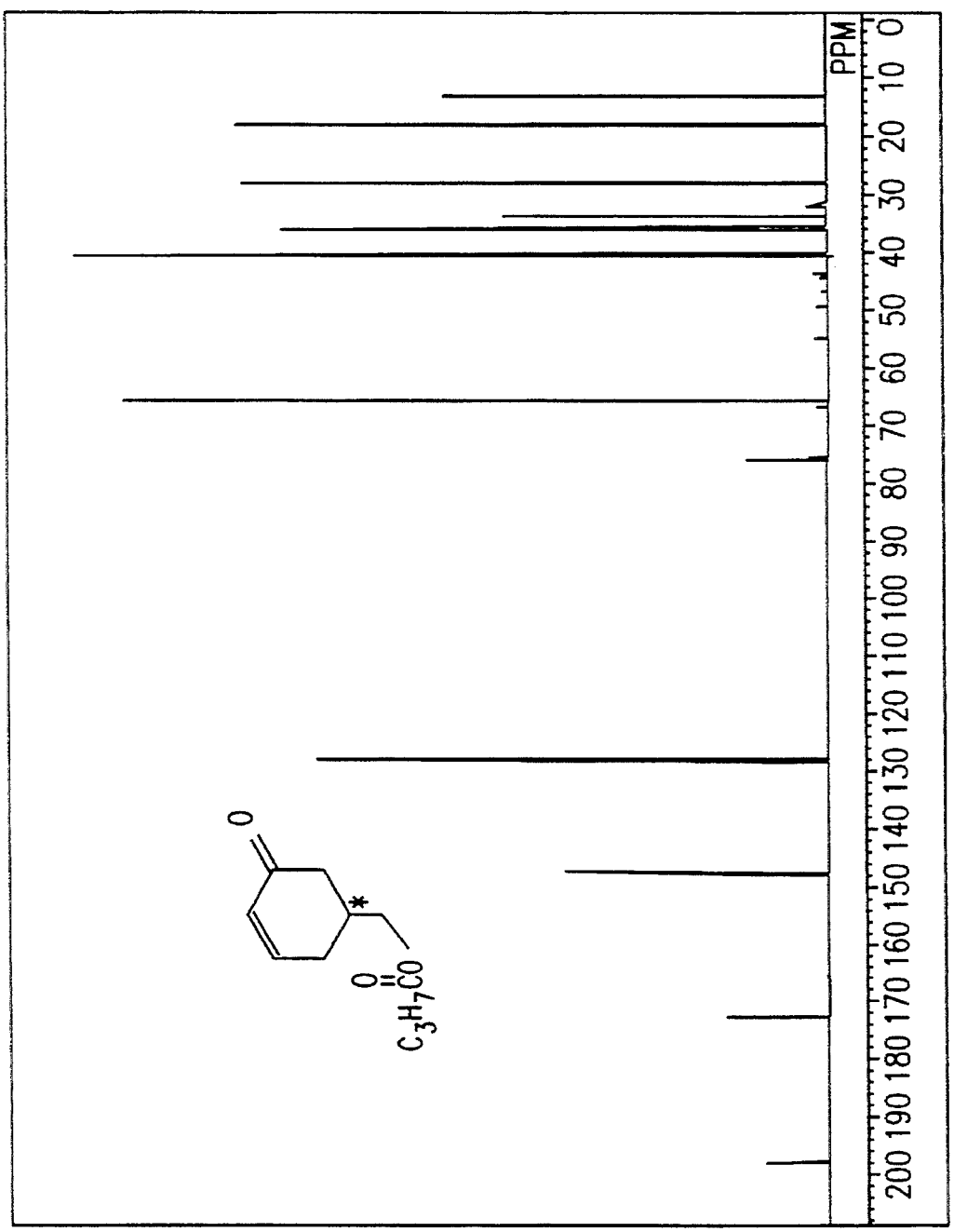
FIG. 3 is a diagram showing the 13 C nuclear magnetic resonance e spectrum of 1-oxo-5-butyroyloxymethyl-2-cyclo-hexene.

Furthermore, the δ-values observed in the 13 C nuclear magnetic resonance spectrum (100 MHz, CDCl3) were 13.5, 18.3, 28.5, 34.5, 35.9, 40.6, 66.6, 129.7, 148.6, 173.3, and 198.1. (See FIG. 3).

It is, therefore, found that this ester is 1-oxo-5-butyroyloxymethyl-2-cyclohexene of the rational formula C11H18O3 and of the structural formula (CF 6).

The following will describe tile method for the production of these esters in detail.

This ester (CF 1) can be obtained by reacting 1-oxo-5-hydroxymethyl-2-cyclohexene (CF 3) with an acid anhydride (CF 4) in an organic solvent under the existence of a lipase.

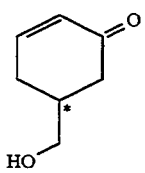
(CF3)

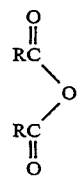
(CF4)

(wherein R is an alkyl group containing 2 to 10 carbon atoms or an aryl group, and mark "*" represents an asymmetric carbon atom).

Examples of the 1-oxo-5-hydroxymethyl-2-cyclohexene (CF 3) which serves as a starting material of this reaction include its racemic modification which can readily be produced by the method as described in J. Am. Chem. Soc., 78, 4405(1956).

As the organic solvent which is used in this invention, ether-type solvents such as diisopropyl ether arid dibutyl ether, aromatic-type solvents such as toluene and xylene, hydrocarbon-type solvents such as isooctane and heptane, and mixtures thereof can be preferably used with isopropyl ether being more preferred.

Moreover, as tile lipase, Lipase M (derived from Mucor and available from Amano Seiyaku), Lipase OF (derived from Candida and available from Meito Sangyo), Lipase PS (derived form Pseudomonas and available form Amano Seiyaku), Pancreatin F (derived form swine porcine and available from Amano Seiyaku), and mixtures thereof can be preferably used.

As the acid anhydride which is used in this reaction, anhydrides or straight-chain carboxylic acids such as propionic acid and butyric acid, anhydrides of branched-chain carboxylic acids such as isobutyric acid, anhydrides of aromatic carboxylic acids such as benzoic acid, mixtures thereof can be preferably used.

To give a full description, the conversion rates and optical purities are shown in Table 1, which were obtained when these acid anhydrides and the above-described various lipases were used.

TABLE 1

| Name of Lipase | Acid dehydrate *(R) | Rate of Yield | Purity |
| --- | --- | --- | --- |
| Lipase M | n—C3H7 | 50% | 16% e. e |
| Lipase OF | n—C3H7 | 100% | 0% e. e |
| Lipase PS | n—C3H7 | 100% | 0% e. e |
| Pancreatin F | n—C3H7 | 100% | 0% e. e |
| Lipase M | iso—C3H7 | 100% | 0% e. e |
| Lipase OF | iso—C3H7 | 60% | 0% e. e |
| Lipase PS | iso—C3H7 | 98% | 0% e. e |
| Pancreatin F | iso—C3H7 | 97% | 0% e. e |
| Lipase M | iso—C6H5 | 65% | 0% e. e |
| Lipase OF | iso—C6H5 | 70% | 0% e. e |
| Lipase PS | iso—C6H5 | 50% | 0% e. e |

Mark "*" represents an R Group in acid dehydrate indicated by (R CO)2O.

The substrate concentration in this reaction is preferably in the range of 1% to 20%; the reaction temperature is preferably in the range of 0° C. to 50° C.; and the reaction time is preferred to be about 2 to 24 hours.

In this way, the ester (CF 1) is produced.

The following will describe the method in detail, in which the ester (CF 1) thus obtained is hydrolyzed to obtain 1-oxo-5-hydroxymethyl-2-cyclohexene (CF 3).

This method includes such a process that the ester (CF 1) is hydrolyzed by its reaction ill a potassium-phosphate buffered aqueous solution or the like, under the existence of a lipase, thereby obtaining 1-oxo-5-hydroxymethyl-2-cyclohexene.

This reaction can be preferably conducted at a reaction temperature of 0° C. to 30° C. for a reaction time of about 1 to 24 hours.

Moreover, as the lipase which is used in this reaction, Lipase M (derived from Mueor and available from Amano Seiyaku), Lipase OF (derived from Candida and available from Meito Sangyo), Lipase PS (derived form Pseudomonas and available form Amano Seiyaku), Panereatin F (derived form swine porcine and available from Amano Seiyaku), and mixtures thereof can be preferably used. This reaction is such a reaction that proceeds in a substantially quantitative manner.

In this way, the ester (CF 1) can readily be hydrolyzed to form 1-oxo-5-hydroxymethyl-2-cyclohexene (CF 3).

Therefore, this ester (CF 1) can be converted, when necessary, into 1-oxo-5-hydroxymethyl-2-cyclohexene (CF 3), which is utilized as an intermediate for the synthesis or various substances.

Furthermore, because it is possible to measure the optical purity of the ester (CF 1) with ease and accuracy, the ester (CF 1) can be utilized for the determination of the optical purity of 1-oxo-5-hydroxy-methyl-2-cyclohexene (CF 3).

For example, 1-oxo-5-hydroxymethyl-2-cyclohexene (CF 3) is used in a method as shown in Table 1 above, with the selection of conditions for allowing the reaction to proceed at the conversion rate of 100% (e.g., a combination of burytic anhydride and Lipase OF), thereby obtaining the ester (CF 1).

The ester (CF 1) is separated into the (5S)-optically-active substance and (5R)-optically-active substance by high-performance liquid chromatography.

As a column which is used in the process for separation by liquid chromatography, CHIRALCEL OB (available from Daiseru Co.) or the like is illustrative of such a column.

For this measurement, a UV detector or the like can be preferably used. Also, as an eluent, hexene/isopropyl alcohol can be preferably used.

By calculating the ratio of the (5S)-optically-active substance to the (5R)-optically-active substance, both of which are separated from each other in such a manner, the optical purity of 1-oxo-5-hydroxymethyl-2-cyclohexene (CF 3) which is a starting material for the synthesis of the ester (CF 1), and the optical purity of 1-oxo-5-hydroxymethyl-2-cyclohexene (CF 3) which is obtained by the hydrolysis of the ester (CF 1) can be determined.

If the above-described process for hydrolysis is conducted with the optically-active ester separated by this liquid chromatography, for example, (5S)-ester (CF 2) wherein the configuration at position 5 is in the S-form, it is possible to obtain (5S)-1-oxo-5-hydroxymethyl-2-cyclo-hexene (CF 5) with ease.

The following will describe the examples of this invention to further clarify the effects of this invention.

EXAMPLES (Example 1)

An example of the synthesis of 1-oxo-5-butyroyloxymethyl-2-cyclohexene

Racemic 1-oxo-5-hydroxymethyl-2-cyclohexene (0.5 g, 4.55 mmol), Lipase OF (1.00 g), and n-butyric anhydride (0.72 g, 4.55 mmol) were mixed and suspended in isopropyl ether (25 ml), followed by vigorous stirring at 23° C. for 24 hours. The reaction mixture was filtered through cerite and the filtrate was concentrated. The residue was purified by0column chromatography (SiO2, 20 g, hexane:EtOAc=9:1–1:1) to give 0.89 g of 1-oxo-5-butyroyloxymethyl-2-cyclohexene (yield: 99% or more).

The results of the elementary analysis were as follows: found: C, 67.15%; H, 8.20%; calcd: C, 67.32%; H, 8.22%.

Moreover, the absorption wave numbers (cm−1) observed in the infrared absorption spectrum were 3025 (w), 2950 (s), 2860 (s), 2820 (w), 1725 (s), 1675 (s), 1610 (w), 1455 (m), 1425 (m), 1380 (s), 1300 (m), 1240 (s), 1170 (s), and 1090 (s). (See FIG. 1). The measurement was conducted by the thin-film method.

The δ-values observed in the proton nuclear magnetic resonance spectrum (400 MHz, CDCl3) were 0.936 (3H, t, J=7.3 Hz), 1.641 (2H, tq, J=7.6, 7.6 Hz), 2.12–2.32 (4H, m), 2.40–2.56 (3H, m), 4.40 (2H, dd, J=5.6, 0.5Hz), 6.02–6.06 (1H, m), and 6.93–6.98 (1H, m). (See FIG. 2).

Furthermore, the δ-values observed in the 13 C nuclear magnetic resonance spectrum (100 MHz, CDCl3) were 13.5, 18.3, 28.5, 34.5, 35.9, 40.6, 66.6, 129.7, 148.6, 173.3, and 198.1. (See FIG. 3).

(Example 2)

An example of the synthesis of 1-oxo-5-butyroyloxymethyl-2-cyclohexene.

Racemic 1-oxo-5-hydroxymethyl-2-cyclohexene (0.5 g, 4.55 mmol), Lipase M (1.00 g), and n-butyric anhydride (0.36 g, 2.28 mmol) were mixed and suspended in isopropyl ether (25 ml), followed by vigorous stirring at 23° C. for 24 hours. The reaction mixture was filtered through cerite and the filtrate was concentrated. The residue was purified by column chromatography (SiO2, 20 g, hexane:EtOAc=9:1–1:1) to give 0.46 g of 1-oxo-5-butyroyloxymethyl-2-cyclohexene (yield: 50%).

The results of the analysis of this substance were the same as those of the analysis of Example 1.

The sample of 1-oxo-5-butyroyloxymethyl-2-cyclohexene, thus obtained, was subjected to the subsequent test of Example 3 below, and it was determined whether the sample contained a greater amount of (5S)-optically-active substance or whether the sample contained a greater amount of (5R)-optically-active substance, so that the optical purity thereof was measured.

(Example 3)

The sample of 1-oxo-5-butyroyloxymethyl-2-cyclohexene, obtained in Example 2, was separated under the following conditions and the optical purity thereof was measured.

Figure 4:
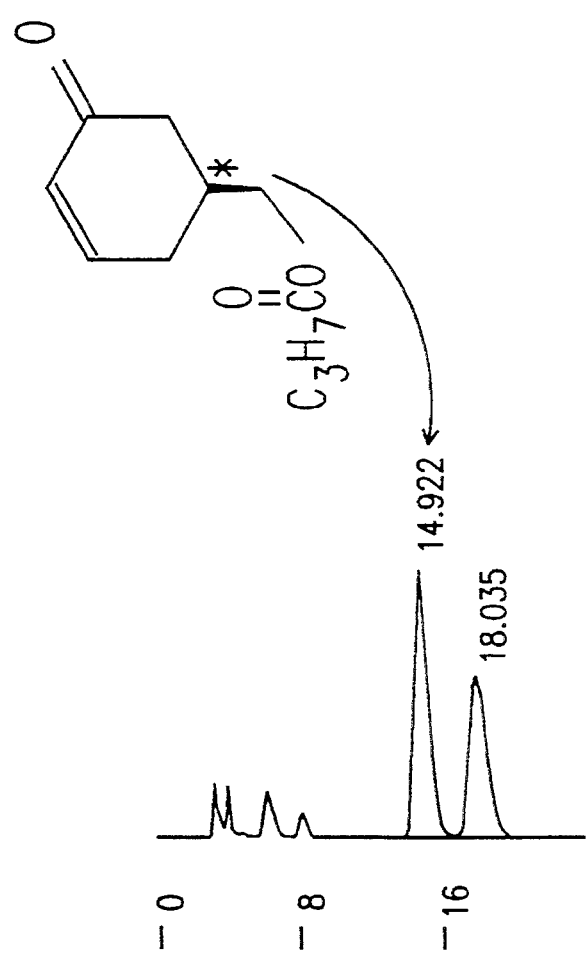
FIG. 4 is a chart of the high-performance liquid chromatography of (5S)-1-oxo-5-butyroyloxymethyl-2-cyclo-hexene.

HPLC (High-Performance Liquid Chromatography) Column: CHIRALCEL OB (manufactured by Daiseru Co.) 0.46×25 cm Eluent: hexane/isopropyl alcohol- 85/15 Temperature: room temperature Detection wave length: 230 nm Retention time: (5S)-form, 14.9 min (5R)-form, 18.0 min From the results of this measurement, it was found that the sample of 1-oxo-5-butyroyloxymethyl-2-cyclohexene was (5S)-1-oxo-5-butyroyloxymethyl-2-cyclohexene because of its higher content of (5S)-optically-active substance, and the optical purity thereof was 16% e.e. (See FIG. 4).

Moreover, the value of specific rotatory power for this product was +10.6 (c=2.0, CHCl3), and from the result of the comparison between the sign of this angle of rotation and the standard data, it was also confirmed that the sample was (5S)-1-oxo-5-butyroyloxymethyl-2-cyclohexene.

(Example 4)

The ester obtained in Example 1 was hydrolyzed under the following conditions.

1-oxo-5-butyroyloxymethyl-2-cyclohexene (0.7 g, 3.57 mmol) and Lipase M (0.7 g) were suspended in potassium-phosphate buffer solution (50 ml) and stirred at 23° C. for 5 hours. The mixture was filtered through cerite and the filtrate was extracted with ether. The ether layer was dried over sodium sulfate, and then concentrated. The residue was purified by column chromatography (SiO2, 20 g, hexane: EtOAc=9:1–1:1) to give 0.39 g (yield 99%) of 1-oxo-5-hydroxy-methyl-2-cyclohexene.

The absorption wave numbers (cm−1) observed in the infrared absorption spectrum of this product were 3400 (brs), 3040 (w), 2900 (s), 1670 (s), and 1380 (s).

It was, therefore, confirmed that this product is 1-oxo-5-hydroxymethyl-2-cyclohexene.

Furthermore, the ester obtained in Example 2 was also hydrolyzed under the same conditions and the absorption wave numbers were observed in the infrared absorption spectrum.

The results were the same as those obtained for the ester of Example 1.

EFFECTS OF THE INVENTION

The novel ester, the method for the production of the same, the process for hydrolysis and the method for the determination of an optical purity using this ester are a novel ester which is an esterified products of 1-oxo-5-hydroxymethyl-2-cyclohexene; a method for the production of the ester, characterized in that 1-oxo-5-hydroxymethyl-2-cyclohexene is esterified in an organic solvent with an acid anhydride and a lipase; a process for the hydrolysis of the novel ester with a lipase to obtain 1-oxo-5-hydroxymethyl-2-cyclohexene; and a method for the determination of an optical purity, characterized in that the optical purity of the ester is measured to determine the optical purity of the 1-oxo-5-hydroxymethyl-2-cyclohexene, respectively, whereby this novel ester is an important intermediate for the synthesis of various natural products, which has high stability, and the optical purity of which can readily be determined.

What is claimed is:

1. A novel ester of the formula:

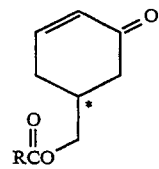
(CF1)

wherein R is an alkyl group containing 2 to 10 carbon atoms or an aryl group, and mark "*" represents an asymmetric carbon atom.

2. A novel ester as set forth in claim 1, characterized in that the ester is an optically-active substance (CF 2) in which the configuration at position 5 is in the S-form:

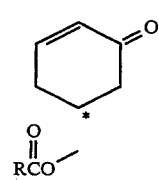
(CF2)

wherein R is an alkyl group containing 2 to 10 carbon atoms or an aryl group, and mark "*" represents an asymmetric carbon atom, and the configuration at position 5 is in the S-form 3. A method for the production of a novel ester of the formula

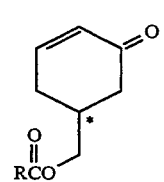
(CF1)

wherein R is an alkyl group containing 2 to 19 carbon atoms or an aryl group, and mark "*" represents an asymmetric carbon atom, which comprises esterifying 1-oxo-5-hydroxy-methyl-2-cyclohexene (CF 3) in an organic solvent with an acid anhydride of the formula (CF 4):

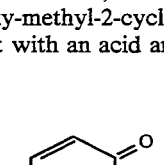
(CF3)

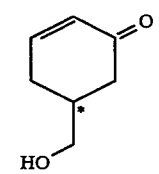
(CF4)

wherein R is an alkyl group containing 2 to 10 carbon atoms or an aryl group, and mark "*" represents an asymmetric carbon atom and a lipase.

4. A method for the production of a novel ester as set forth in claim 3, characterized in that said lipase is one or more kinds of lipases selected from the group consisting of Lipase M (derived from Mucor), Lipase OF (derived from Candida), Lipase PS (derived from Pseudomonas), and Pancreatin F (derived from swine porcine).

5. A method for the production of a novel ester as set forth in claim 3, characterized in that said organic solvent is one or more kinds of organic solvents selected from the group consisting of ether-type, aromatic-type, and hydrocarbon-type organic solvents.

6. A method for the production of a novel ester as set forth in claim 4, characterized in that said organic solvent is one or more kinds of organic solvents selected from the group consisting of ether-type, aromatic-type, and hydrocarbon-type organic solvents.

7. A process which comprises hydrolyzing a novel ester of the formula

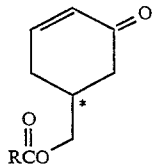

(CF1)

wherein R is an alkyl group containing 2 to 10 carbon atoms or an aryl group, and mark "*" represents an asymmetric carbon atom, with a lipase to give 1-oxo-5-hydroxymethyl-2-cyclohexene (CF 3).

8. A method for the determination of an optical purity, characterized in that the optical purity of said optically-active ester (CF 1) as recited in claim 1 is measured to determine the optical purity of said 1-oxo-5-hydroxymethyl-2-cyclohexene (CF 3).

* * * * *